United States Patent [19]

Sayles

[11] 3,980,710
[45] Sept. 14, 1976

[54] METHYLTRICARBORANYLMETHYL PERCHLORATE

[75] Inventor: David C. Sayles, Huntsville, Ala.

[73] Assignee: The United States of America as represented by the Scretary of the Army, Washington, D.C.

[22] Filed: Dec. 23, 1974

[21] Appl. No.: 535,333

[52] U.S. Cl. .......................... 260/606.5 B; 149/22
[51] Int. Cl.$^2$ .......................................... C07F 5/02
[58] Field of Search ............... 260/606.5 B; 149/75, 149/22

[56] References Cited
UNITED STATES PATENTS

| | | | |
|---|---|---|---|
| 3,427,297 | 2/1969 | Chaille et al. | 149/75 X |
| 3,660,455 | 5/1972 | Hoffman | 149/75 UX |

Primary Examiner—Leland A. Sebastian
Attorney, Agent, or Firm—Nathan Edelberg; Robert P. Gibson; Jack W. Voigt

[57] ABSTRACT

Methyltricarboranylmethyl perchlorate is disclosed along with its synthesis and its use in a solid composite propellant. Three carboranyl groups and a perchlorate group are contained in the intramolecular perchlorate salt, methyltricarboranylmethyl perchlorate, which is used as a partial replacement for ammonium perchlorate and as a replacement for liquid carborane catalyst-plasticizer compounds to achieve ultrahigh burning rates for propellants. The perchlorate salt when incorporated into a propellant composition contributes to the oxidizer function, and in addition, since three carboranyl groups are present in each molecule of the salt, the burning rate catalysis function is accomplished without having to incorporate separate burning rate catalysts.

1 Claim, No Drawings

METHYLTRICARBORANYLMETHYL PERCHLORATE

DEDICATORY CLAUSE

The invention described herein may be manufactured, used, and licensed by or for the Government for governmental purposes without the payment to me of any royalties thereon.

BACKGROUND OF THE INVENTION

Carboranes and derivatives thereof have been and are being used as burning rate catalysts for solid propellant compositions. Normal-hexylcarborane and carboranylmethyl, -ethyl or -propyl sulfide are typical carborane derivatives which are catalyst-plasticizer compounds that have been used for high burning rate propellants.

Inorganic and organic iron and iron-containing compounds have also been employed in propellants as burning rate catalysts. Ferrocene and ferrocene derivatives are typical of the organoiron compounds which have been used as burning rate catalysts.

Various theories and proposed mechanisms for the acceleration of propellant burning rates have evolved from experimentation in the field of catalysis. Apparently, the rate-controlling step for uncatalyzed propellant burning rates is determined mainly by the rate at which ammonium perchlorate undergoes decomposition. The burning rates of propellants increase as the particle size of ammonium perchlorate catalyst-plasticizer reduced. Smaller particle sizes facilitate the decomposition rate of ammonium perchlorate.

Very fine particle-sized (e.g. of only a few microns average mean-weight-diameter particle size) ammonium perchlorate in conjunction with catalysts (which have been incorporated in the propellant composition as liquid plasticizers) have been responsible for achieving ultrahigh burning rates for propellant compositions. The use of the liquid-type burning rate catalysts, however, has lead to other problems which include catalyst-plasicizer migration into the liner-insulation system.

The migration of liquid catalysts into the liner-insulation material can be eliminated by the use of a mixed intramolecular perchlorate salt: carboranyldiferrocenylmethyl perchlorate. The salt was disclosed and claimed in my U.S. patent application Ser. No. 120,682, filed Mar. 3, 1971. The activity of the compound is attributed to two different mechanisms for burning rate catalysis plus the oxidizer function which is derived from the perchlorate.

A combination catalyst and oxidizer ingredient which could be used as a replacement for a liquid carborane catalyst-plasticizer, and which could be used as a partial replacement for ammonium perchlorate without reducing the perchlorate ion content in the propellant would be highly desirable, particularly, if the catalyst-oxidizer ingredient is a solid ingredient of low explosive sensitivity and has excellent compatibility with the other propellant ingredients.

Therefore, an object of this invention is to provide a propellant ingredient which serves as a combined catalyst and oxidizer and which includes the carboranyl functional group.

Another object of this invention is to provide a catalyst-oxidizer propellant ingredient which includes the carboranyl catalyst material as the major part of the solid ingredient and which overcomes the problem of catalyst-plasticizer migration into the liner-insulation system.

Still a further object of this invention is to provide an oxidizer-catalyst ingredient which will permit the use of a lesser total amount of catalyst and ammonium perchlorate in a propellant formulation, and thereby permit the use of a larger quantity of binder, and/or fuel, and/or oxidizer in the formulation to yield a propellant of high solids (metallic fuel, inorganic oxidizer) loading without adversely affecting the mechanical properties which is the situation which normally arises when the solids loading of a propellant is increased.

SUMMARY OF THE INVENTION

Methyltricarboranylmethyl perchlorate serves as a partial replacement for the ammonium perchlorate oxidizer of a composite propellant formulation to achieve high burning rates of the composition. Methyltricarboranylmethyl perchlorate contains a single catalyst ingredient, the carboranyl group, in three positions to each perchlorate group as part of the intramolecular structure of a solid salt. The solid salt is synthesized from decaborane by a series of reactions by first converting decaborane to carboranylcarbonitrile by reaction with acetonitrile. The carboranylcarbonitrile is reacted with carboranyllithium (which is prepared by the reaction of decaborane with acetylene, followed by lithiation) to form the methyldicarboranylketone which is reacted with an additional quantity of carboranyllithium to form, upon hydrolysis, the methyltricarboranylmethyl alcohol. The alcohol is reacted with perchloric acid to form the methyltricarboranylmethyl perchlorate which is a solid intramolecular solid salt containing three carboranyl functional groups and a perchlorate functional group. The solid salt provides, in addition to oxidizer functions, catalytic functions by way of the carboranyl groups near the decomposition site of the perchlorate radical which is the oxidizer moiety of the molecule. Thus, the proven catalytic value of the carboranyl ion is available for use in the solid propellant composition without the undesirable migration problems associated with some of the liquid type carboranyl plasticizers.

DESCRIPTION OF THE PREFERRED EMBODIMENT

The synthesis of methyltricarboranylmethyl perchlorate can be accomplished by the following series of chemical steps, similar to the procedure described by A. N. Nesmeyanov, E. G. Perevalora, L. I. Leont'eva and Yu. A. Ustynyuk, Izvestia Akademii Nauk U.S.S.R., Scriya Khimcheskaya No. 3, pp 556–558, March 1966. It can be summarized by the following series of chemical equations:

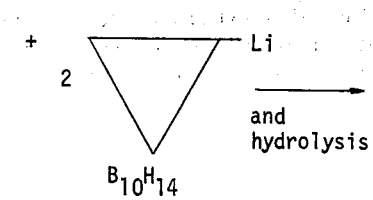

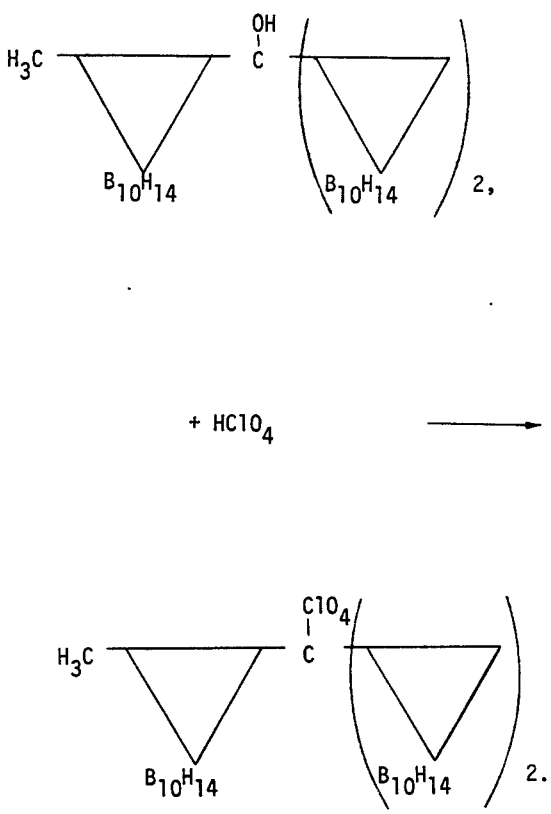

Synthesis of methyltricarboranylmethyl perchlorate involves the following: Decaborane is converted to carboranylcarbonitrile by reaction with acetonitrile. The carboranylcarbonitrile is reacted with carboranyllithium to form the methyldicarboranylketone which is reacted with an additional quantity of carboranyllithium to form the methyltricarboranylmethyl alcohol upon hydrolysis. The alcohol is reacted with perchloric acid to form the methyltricarboranylmethyl perchlorate.

The use of methyltricarboranylmethyl perchlorate in a composite propellant provides a means for simultaneously introducing a burning rate catalyst as part of a perchlorate-type oxidizer. This is illustrated in the following propellant compositions. Composition A depicts a propellant composition which has been especially developed as a high burning rate propellant as a possible alternate for the Safeguard System. Composition B depicts a comparable propellant which contains the methyltricarboranylmethyl perchlorate. The carboranyl content is maintained the same in both compositions. (Table I)

The following conclusions are possible:

a. Because Composition B contains the same percentage of carboranyl moiety as Composition A, the burning rate will be nearly comparable. In actuality, it was found to increase the burning rate.

b. Because a lesser amount of methyltricarboranylmethyl perchlorate is required to produce the same catalytic content, a larger amount of the hydroxyl-terminated polybutadiene prepolymer could be used. This would mean improved mechanical properties and processing characteristics.

c. If a lesser amount of hydroxyl-terminated polybutadiene prepolymer than that which is contained in Composition B were used, this would permit the use of a higher percentage of aluminum and ammonium perchlorate and result in higher performance as well as better mechanical properties.

d. Since the presently-used n-hexylcarborane (see Composition A) is liquid, it undergoes migration into the liner-insulation system. This migration problem does not exist in Composition B because the burning rate promoter is a solid salt.

TABLE I

| A COMPARISON OF PROPELLANTS CONTAINING CARBORANYL BURNING RATE PROMOTERS | | |
|---|---|---|
| | COMPOSITION A | COMPOSITION B |
| INGREDIENTS: (Wt %) | | |
| Hydroxyl-terminated Polybutadiene Prepolymer | 6.05 | 14.75 |
| Isophorone Diisocyanate | 0.50 | 1.50 |
| Bonding Agent (BA-114) | 0.35 | 0.35 |
| Normal Hexylcarborane | 13.10 | — |
| Methyltricarboranylmethyl perchlorate | — | 10.7 |
| Ammonium Perchlorate | 70.0 | 62.7 |
| Aluminum (H-30) | 10.0 | 10 |
| BALLISTIC PROPERTIES: | | |
| Isps (lbf-sec/lbm)(15° half angle) (1000/14.7 psia) | 255 | 255 |
| Ispsd (in 6-in motor) (lbf-sec/lbm) | 245 | 250 |
| Pressure Exponent (n) | 0.65 | 0.57 |
| Burning Rate (at 2000 psia) (ips) | 5.7 | 8–9 |
| MECHANICAL PROPERTIES: | | |
| Specific Gravity (gm/cc) | 1.63 | 1.64 |
| Stress/Strain (psi/%) | | |
| —40°F | 330/20 | Not Determined |
| +77°F | 150/30 | 225/40 |
| +140°F | 120/35 | Not Determined |
| Modulus (psi) | 600–700 | 1200–1300 |

I claim:

1. Methyltricarboranylmethyl perchlorate.

* * * * *